United States Patent [19]

Muto

[11] Patent Number: 4,475,548
[45] Date of Patent: Oct. 9, 1984

[54] FITTING FOR ENDOTRACHEAL TUBE APPARATUS AND METHOD OF MAKING THE FITTING

[76] Inventor: Rudolph Muto, 24 William St., Andover, Mass. 01810

[21] Appl. No.: 383,968

[22] Filed: Jun. 1, 1982

[51] Int. Cl.³ .......................................... A61M 25/02
[52] U.S. Cl. ............................... 128/207.14; 128/912; 604/167
[58] Field of Search ................. 604/175, 167, 256, 44, 604/43, 99, 86, 148, 244; 128/207.14, 633, 634, 912; 215/247, DIG. 3; 277/237

[56] References Cited

U.S. PATENT DOCUMENTS

| | | | |
|---|---|---|---|
| 3,097,646 | 7/1963 | Scislowicz | 604/167 |
| 3,853,127 | 12/1974 | Spademan | 604/167 |
| 4,149,535 | 4/1979 | Volder | 604/43 |
| 4,351,328 | 9/1982 | Bodai | 128/207.15 |

*Primary Examiner*—Henry J. Recla
*Assistant Examiner*—Karin M. Reichle
*Attorney, Agent, or Firm*—Pearson & Pearson

[57] ABSTRACT

A fitting for endotracheal apparatus to receive an endoscopic tube or the like comprises a sleeve in which a slit through foam body is encompassed and seized under longitudinal compression, radial compression at the inner end and partially relieved pressure at the outer end. The foam body is normally of bell, or mushroom, shape with an elongated cylindrical shank rounded inner end, flat outer end and an enlarged diameter lip at the outer end. The sleeve includes a head joined to a tapered stem by a truncated conical, inward flared section, the head having a circular outer edge. A cap having an annular top rim defining a central opening, has an integral skirt fitted tightly around the head so that the foam body is compressed longitudinally between the annular rim of the cap and the inward flared section of the sleeve. It is compressed radially by the inward flared section and the pressure is relieved at the opening in the cap by the foam protruding into the opening and into the space between the cap rim and the edge of the head.

4 Claims, 5 Drawing Figures

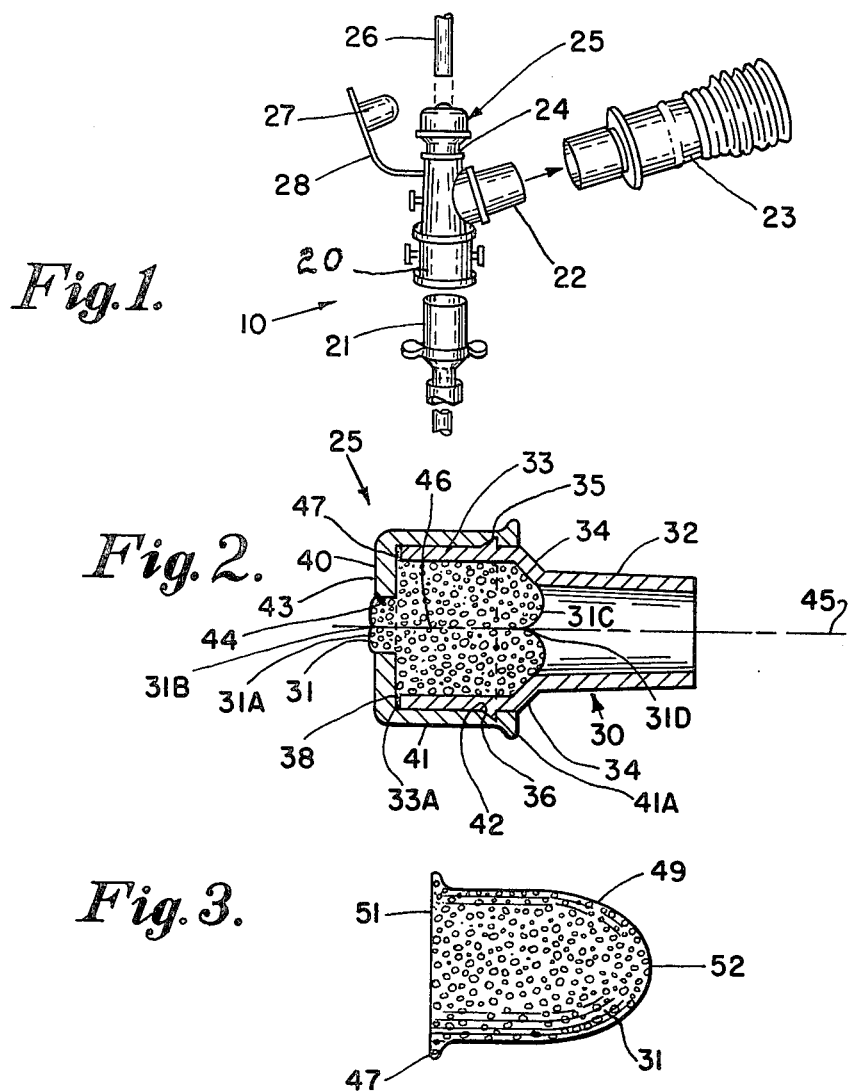
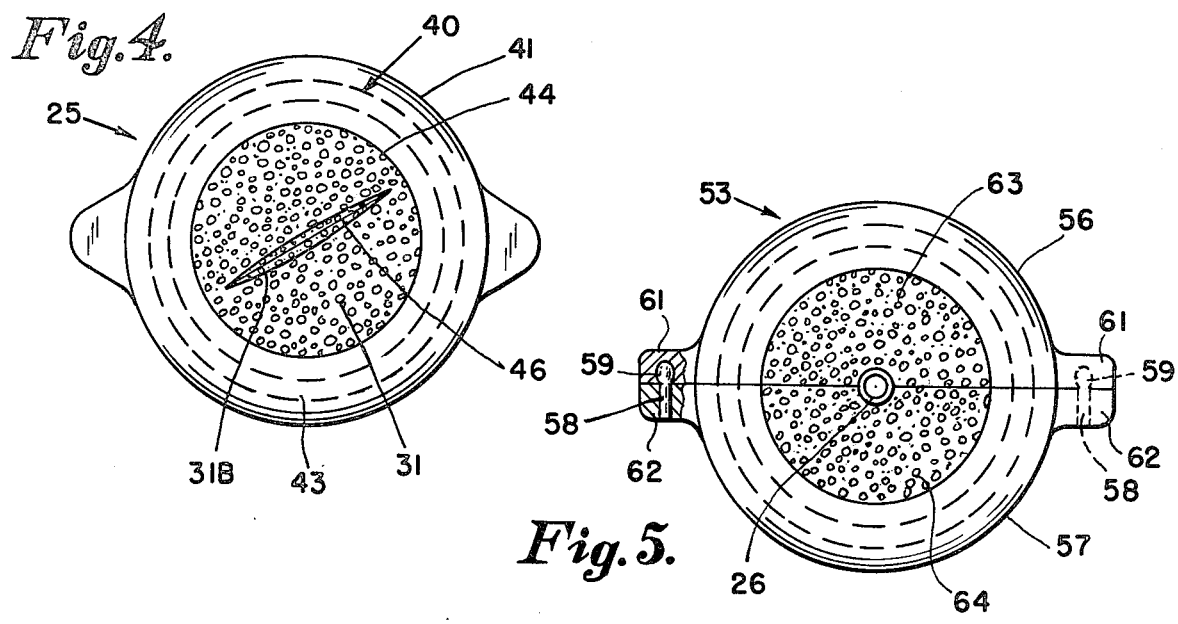

FITTING FOR ENDOTRACHEAL TUBE APPARATUS AND METHOD OF MAKING THE FITTING

BACKGROUND OF THE INVENTION

The present invention is related to medical apparatus and more particularly to a fitting for endotracheal tube apparatus to receive an endoscopic tube or the like, for example, an endoscopic tube or a tube for aspiration of liquid from the lungs.

Endotracheal apparatus is used for various ailments and for diagnostic purposes. Heretofore the fitting for endotracheal apparatus may include, for example, a diaphragm in which is centrally located a walled aperture which is to receive the endoscopic tube (which may not be a tube in fact, but an optical fiber bundle) or an aspirator tube, or the like.

In U.S. Pat. No. 3,388,705 to Grosshandler June 18, 1968 for Universal Endotracheal Tube Coupling or Adaptor, a fitting or adaptor is provided in which a diaphragm with a central walled aperture is provided to receive in fluid tight relation a tube applying gas to the endotracheal tube. U.S. Pat. No. 4,152,017 to Abramson May 1, 1979, for Swivel Connector for Endotracheal Tube or the Like discloses an endotracheal tube assembly or apparatus with a swivel connector for the endotracheal tube. U.S. Pat. No. 3,667,475 to Venturelli et al June 6, 1972, for Endo-Tracheal tube adaptors for Use in Administering Gases shows a centrally apertured walled diaphragm in which a tube may be inserted to administer gas. U.S. Pat. No. 3,643,653 to Takahashi et al Feb. 22, 1972 for Endoscopic Apparatus shows endotracheal apparatus in which a seal is secured between a minor endoscope and a major endoscope by using an O-ring. In the use of diaphrams of this type, the sensitive outer surface of the fiber optic bundle tubes may be damaged during operation, thus adversely affecting their operation. They are easily scratched, which often affects their optical capabilities. They are easily broken during manipulation, and expensive to replace.

SUMMARY OF THE INVENTION

In accordance with the invention, a fitting to receive an endoscopic tube or the like comprises a cellular foam body having two ends, a longitudinal end-to-end axis, one or more cylindrical portions coaxial with the axis, and an end-to-end through slit, and a coaxial sleeve arrangement encompassing and seizing the foam body under compressive stress, so that the tube or the like, when used within the foam body slit is surrounded by and compressively held by the foam body. The cellular foam body is preferably formed of a material, such as surgical rubber, which is physiologically inert and may be wet with a saline solution to facilitate the sliding of the tube contained in the slit. The foaming is preferably of the "open" cell type to facilitate wetting and to enable the foam body to hold and absorb the liquid.

DESCRIPTION OF THE DRAWING

The various objects, advantages, and novel features of the invention will be more fully understood by reading the following detailed description in conjunction with the accompanying drawing, in which like reference numerals refer to like parts, and in which:

FIG. 1 is a schematic view of an endotracheal apparatus carrying an endoscopic tube;

FIG. 2 is a transverse, cross-sectional view of a fitting of FIG. 1 which embodies the invention and through which the endoscopic tube is inserted;

FIG. 3 is a longitudinal cross-sectional view of the foam body of the fitting of FIG. 2 before its insertion;

FIG. 4 is an enlarged end view of the fitting of the invention; and

FIG. 5 is a view similar to FIG. 4 of another embodiment.

DESCRIPTION OF A PREFERRED EMBODIMENT

Referring to FIG. 1, an endotracheal tube assembly 10 includes an endotracheal tube 21, having a swivel junction 22 leading to a tube 23 for connection to a respirator or pump, and provided with a swivel joint 20 relative to the tube 21. An adapter, or fitting, 25 fits into the passageway, or bore, 24 and an endoscopic fiber optic or suction catheter tube 26 or the like passes through the fitting 25 in fluid sealing relation through the swivel joint 20 and on through the endotracheal tube 21. The bore 24 may be closed by a tapered plug 27 carried on flexible band 28 when the adapter, or fitting 25 has served its purpose.

The fitting 25 is illustrated in greater detail in FIG. 2 and FIG. 4. A foam body 31 is embraced or encompassed and seized within a sleeve 30 having a proximal (as viewed from the patient) tapered stem 32 and an attached larger diameter head 33 joined to the stem 32 by a flared section 34. An external circumferential ridge 35 near the proximal end of the head 33 has a slope 36 smoothly and progressively increasing in diameter from distal toward proximal end of the stem 32. The ridge 35 terminates at its proximal end in an abrupt radial plane or edge. The head 33 terminates or is cut off distally at an end edge 33A.

A cap 40 has a skirt 41 which fits over the head 33 and is staked by the ridge 35 thereto. The skirt 41 may have formed therein (or the effect of staking on the ridge 35 may form) internally near the proximal end of skirt 41, a groove 42 which retains with the skating ridge 35 of the head 33 in place. The cap 40 has a top 43 with the central opening 44. The foam body 31 is enclosed within the head 33 and also held therein in compressive stress by the top 43. The head 33 and stem 32 have bores coaxial with a central axis 45, and the internal bore of the skirt and the central aperture are also coaxial with the same axis 45.

The foam body is slit end to end, preferably diametrally and preferably not to the edge, by a slit 46. The foam body 31 may be made of any suitable resilient, preferably soft material which is physiologically inert to a patient. A suggested material is surgical rubber which has been appropriately foamed. The foaming should be of the type which is known as "open", that is, the foamed spaces communicate, and are open (not forming enclosed spaces) as in a natural sponge, so that they tend to absorb liquid. Initially as shown in FIG. 3, the foam body 31 should be somewhat larger in diameter than the internal diameter of the head 33, so that the body must be forced into the cylindrical recess 29 in the head 33 by compressing the body 31. The body 31 should also initially be a little longer axially than the recess in the head 33, so that as the skirt 41 is brought over the head 33 with the inserted body 31 inside, the peripheral rim 38 of top 43 compresses the foam body 31 axially. Thus, the foam body is compressed both radially and axially.

The body 31 may have a cylindrical shank 49 of reduced diameter, a flat end 51 and an opposite rounded end 52 initially slightly flared in a kind of bell, or mushroom, shape so that the lip 47 of the bell shape overfits the distal edge 33A of the head 33, and the lip 47 is clasped between the edge 33A and the annular rim 38 of the cap as shown in FIG. 2. When completely pushed on the head portion 33, the cap 40 is staked on the ridge 35, the sloping edge 36 functioning as a cam to lift the proximal edge of the skirt 41 over the ridge 35. An external cylindrical slight reinforcement, or bead 41A about the proximal end of the cap skirt 41A insures that the staking is secure and that the skirt does not split or break.

After the parts are together a sharp thin double-edged knife may be inserted through the central opening 44 axially of the body 31 to form the slit 46. Clearly when thus made, the slit does not extend to the sidewalls, since the width of the knife must be less than the diameter of central opening 44. When the body 31 is compressed into place, the compression causes the somewhat spherical part of the bell shape to protrude into the arm portion 32 and also out from the central opening 44 as at 31A. Then when the slit is cut, the pressure is partially relieved locally at the cut near the surface 51, so that the body 31 is slightly dimpled as at 31B. A dimple results at the other end 52 of the body 31 as indicated at 31D in the protrusion 31C. The dimple 31B at the opening 44 is useful as indicating the place at which an endoscope or the like may be inserted.

When the fitting 25 is used, it is usually desirable that it be wet with a saline solution, although the fitting works well dry. When wet as an endoscope or the like is entered, the saline solution affords a degree of lubrication. Thus the instrument may be manipulated more easily and with less danger of scratching the delicate surface of the fiber optic endoscope or the like. Moreover the grasp of the instrument in the soft foam insures that if fluid (gas or liquid) pressure is exerted from either the interior of the arm portion 32 in excess of that at the opening 44, or less than that at the opening 44, the resultant deformation, though slight, of the foam rubber body tends to retain both the slit against the endoscope and the body 31 against the interior walls more tightly than before the pressure differential, thus to insure seal against fluid, either gas or liquid. This surety of seal is most useful. By simply dipping the fitting 25 into a saline solution or a siliconized solution before use, the foam body 31 absorbs the solution which acts as a lubricant for entry and maneuver of an endoscope, catheter or other tube. The solution aids in self-sealing to some degree against air, blood, or other fluid. Thus when a tube is introduced for applying gas or as an aspirator tube, the seal is retained for longer period than would otherwise be possible without the wetting. The use of physiologically neutral materials, such as surgical foam rubber for the body 31, and metal or plastic for the remainder of the fitting 25 avoids pyrogenic or other adverse reactions in the patient. Although as noted the foam body may be used dry, and will seal, the wetting is retained by the spongelike capacity of the body 31 so that the liquid continues to lend its beneficent lubricating and added sealing effects over a substantial period of time without re-wetting.

Other forms of slits may be used, but the one illustrated has been found to be preferable and effective. The slit may be extended to the side walls completely, that is the margins of the foam body 31, entirely or partially along its axial length. Nevertheless the method of cutting the body described above after its insertion is convenient and more readily made to be of appropriate size.

Among other advantages, the fitting or adaptor of the present invention affords easy access to different sizes of endoscopic or other tubes, without the changing fittings, because the softness of the foam body easily and readily expands or contracts as required. Formerly with the walled apertures only few sizes could be accommodated by a particular aperture. The fitting deals more gently than the prior walled apertures, resulting in less damage. Tubes are more easily fed into and drawn out of the soft spongy body, especially when lubricated with a saline solution, than into or out of collars or the like. Fluid seal when required is better maintained than heretofore in this type of apparatus. The ability to thus employ saline or siliconized solutions without frequent wettings further facilitates the use of the fitting of the invention.

As shown in FIG. 5 a fitting 53, similar to fitting 25, may be provided for snap fitting over an endotracheal tube 26, or the like, already in place in the patient, when endwise insertion is not possible and sidewise application is required. In such case the fitting 53 is made in two halves 56 and 57 which snap together around the tube 26 by means of pins 58 and holes 59 in ears 61 and 62 compress the foam 63 and 64, in each half around the tube 26, to seal against passage of blood, etc.

In operation the single use, disposable fiberoptic scope suction catheter adapter fitting 25 is preferably lubricated with a sterile saline solution on the foam body 31 and the fitting 25 is then inserted into the suction port, or bore, 24 of the assembly 10. The assembly 10 is then connected to the ventilator, respirator, or pump 23 and to the 15 mm termination of the endotracheal tube or tracheostomy tube 21.

The fiberoptic scope, or suction catheter, 26 is then inserted in the slit 46 in foam body 31, and down through the tracheal, or tracheostomy tube, with a complete seal and no damage to the surface of the delicate optical fibers or other outer surface.

Following the procedure the fitting 25 and swivel 10 may be discarded and the patient reconnected to the ventilator 23. If desired, the swivel 10 may be left in place and the fitting 25 removed with plug 27 inserted in bore 24.

I claim:

1. A fitting for endotracheal apparatus to receive an endoscopic tube, or the like, said fitting comprising:
    an elongated body of soft resilient cellular foam of generally bell, or mushroom shape, and of predetermined length, having, a flat outer end with a laterally extending enlarged lip therearound, an opposite, rounded inner end and an elongated cylindrical shank, of predetermined diameter between said lip and said rounded end;
    a sleeve having a head with a circular outer end edge, a cylindrical interior recess, an inwardly flared section forming an annular, truncated conical partial closure to said recess and an elongated, hollow tapered stem, said head coaxially encompassing said body in said recess, said lip overlies the circular edge of said sleeve and;
    a cap having an integral skirt fitting around said head and affixed thereto and having a top with an integral, inwardly extending peripheral rim, defining an opening and said lip is clasped between the circular edge and the peripheral rim;

said foam body having a longitudinal slit pre-formed therein from end to end, being under longitudinal compression between said peripheral rim and said flared section, being under radial compression at said flared section and being under a relieved pressure at said opening.

2. A fitting as specified in claim 1 wherein:

said head of said sleeve includes a circumferential ridge extending therearound and the skirt of said cap includes a cooperating groove extending therearound and arranged to clamp said cap on said head under predetermined longitudinal pressure.

3. A fitting as specified in claim 1 wherein:

said foam body is of physiologically inert, open cell, surgical rubber and said sleeve is of inflexible material.

4. A method of making a fitting for endotracheal tube apparatus to receive, seal and reseal an endoscopic tube, or the like, the fitting having an elongated cellular foam body of generally bell shape having a flat outer end with a laterally extending enlarged lip therearound, an opposite round end and an elongated cylindrical shank therebetween a sleeve having a circular outer end edge, a cylindrical recess, an inwardly flared section forming a shoulder section and an elongated, hollow tapered stem and a cap having a top with an integral, inwardly extending peripheral rim defining a central opening which comprises the steps of:

forming the foam body in a circularly symmetrical shape of greater length than said recess;

forcing the body into the recess and shoulder section of the sleeve by affixing the cap over the sleeve with the lip of the body clasped between the circular edge of the sleeve and peripheral rim of the cap to hold the body in permanent longitudinal compression between the top rim and shoulder section and permanent radial compression in the area of the shoulder section; and then preslitting the foam body longitudinally with a through slit, by slitting through said opening.

* * * * *